United States Patent [19]

Zecher et al.

[11] 4,196,274
[45] Apr. 1, 1980

[54] PROCESS FOR THE PRODUCTION OF HYDANTOINS AND POLYHYDANTOIN RESINS

[75] Inventors: Wilfried Zecher; Rudolf Merten, both of Leverkusen, Fed. Rep. of Germany

[73] Assignee: Bayer Aktiengesellschaft, Leverkusen, Fed. Rep. of Germany

[21] Appl. No.: 854,110

[22] Filed: Nov. 23, 1977

[30] Foreign Application Priority Data

Dec. 18, 1976 [DE] Fed. Rep. of Germany ....... 2657560

[51] Int. Cl.² .................... C08G 18/34; C08G 18/67; C07D 401/06; C07D 403/06
[52] U.S. Cl. ........................................ 528/73; 528/75; 544/60; 544/82; 544/139; 544/370; 548/309; 548/310; 548/313
[58] Field of Search ................... 528/75, 73; 548/310, 548/313

[56] References Cited

U.S. PATENT DOCUMENTS

| | | | |
|---|---|---|---|
| 3,549,599 | 12/1970 | Merten | 528/75 |
| 3,684,774 | 8/1972 | Merten et al. | 548/313 |
| 3,705,874 | 12/1972 | Merten et al. | 528/75 |
| 3,817,926 | 6/1974 | Pauze | 528/75 |
| 3,939,122 | 2/1976 | Merten et al. | 548/310 |
| 3,966,683 | 6/1976 | Merten et al. | 548/310 |

*Primary Examiner*—H. S. Cockeram
*Attorney, Agent, or Firm*—Connolly and Hutz

[57] ABSTRACT

An iso(thio)cyanate having at least two iso(thio)cyanate groups is reacted with an unsaturated amido acid at 0°–450° C., said amido acid being a compound of the formula

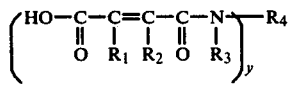

wherein $R_1$, $R_2$, $R_3$ and $R_4$ may be the same or different and each is hydrogen, aliphatic radical, aliphatic-aromatic radical or aromatic radical; $R_1$ and $R_2$ may additionally be halogen and y is an integer from 1–3.

8 Claims, No Drawings

PROCESS FOR THE PRODUCTION OF HYDANTOINS AND POLYHYDANTOIN RESINS

It is known that hydantoins are obtained by reacting α-aminocarboxylic acid derivatives with isocyanates (Am. Chem. J. 45, 383). Another possible method of producing hydantoins is to react α-aminonitriles with isocyanates and to hydrolyse the imino compounds formed into hydantoins.

Whereas monomolecular hydantoins have interesting properties in the pharmaceutical and plant-protection fields, higher molecular weight hydantoins are preferably used as thermally stable plastics materials, particularly in the electrical insulation field (French Pat. No. 1,484,694 = British Pat. No. 1 106 915).

It has now been found that hydantoins can be obtained in good yields by reacting organic isocyanates with unsaturated amido acids corresponding to the general formula:

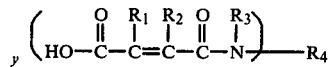

in which $R_1$, $R_2$, $R_3$ and $R_4$ are the same or different and represent hydrogen, an aliphatic, aliphatic-aromatic or aromatic radical, and $R_1$ and $R_2$ may additionally represent halogen, and y is an integer from 1 to 3, perferably 1 or 2, most preferably 2, at temperatures in the range of from 0 to 450° C. and preferably at temperatures in the range of from 0 to 250° C.

The course of the reaction is surprising because by reacting aliphatic carboxylic acids and isocyanates the corresponding acid anhydrides and ureas are predominantly formed. Moreover it had to be expected that the cyclic acid anhydrides, which can be formed from the above-mentioned amido acids by splitting off the amine group, react with isocyanates to form complicated, partly polymeric mixtures of substances. The relatively good yields which even enable polymers to be synthesized was also quite unexpected, because the reaction takes place in several intermediate stages, whereby two vals of isocyanate are being reacted per mole of amido acid for ring formation. In addition, the reaction according to the invention is only accompanied by the liberation of $CO_2$ and not, as in conventional processes for the production of hydantoins, by the liberation of water or alcohols, which can give rise to troublesome secondary reactions.

The unsaturated amido acids used as starting materials in accordance with the invention may be obtained by a simple reaction, for example from the acid anhydrides of unsaturated dicarboxylic acids and primary or secondary monoamines or polyamines, and may be used as such or may even be formed from the components in the reaction medium. It is preferred to use compounds corresponding to the general formula:

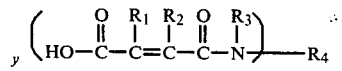

in which $R_1$, $R_2$, $R_3$ and $R_4$ are the same or different and represent hydrogen, an aliphatic radical with 1 to 20 carbon atoms, an aliphatic-aromatic radical with 7 to 20 carbon atoms or an aromatic radical with 4 to 20, preferably 6–16, carbon atoms, and $R_1$ and $R_2$ may additionally represent halogen such as fluorine, chlorine, and y has the same meaning as above.

The radicals $R_1$ and $R_2$ are derived for example from hydrogen, fluorine, chlorine, bromine, methane, ethane, hexane, cyclohexane, propene, toluene and benzene and in addition may together form a ring with up to 8 carbon atoms. The radicals $R_3$ and $R_4$ are derived for example from hydrogen, methane, ethane, n-, iso or tert.-butane, hexane, eicosane, propene, butane, cyclohexane, benzene, naphthalene, diphenyl methane, diphenyl ether, diphenyl sulphone, ω- or nucleus-substituted toluene, xylene, polyethers, polyesters, polyureas and polyurethanes and may be substituted once or several times, for example by halogen or alkyl group radicals, carboxylic acid, carboxylic ester, hydroxy and amino radicals. In addition, $R_3$ and $R_4$ may together form a heterocyclic radical with 3 to 7 carbon atoms which, in addition to the nitrogen, may contain further hetero atoms, such as, for example, nitrogen, oxygen or sulphur. Examples of the cyclic radical

are pyrrolidine, imidazoline, piperidine, morpholine, thiomorpholine and piperazine which may be substituted by another unsaturated carboxylic acid radical defined above.

Preferably, $R_1$ and $R_2$ represent hydrogen and $R_3$ and $R_4$, which may be the same or different, represent hydrogen, an aliphatic radical with 1 to 6 carbon atoms, an aromatic radical with 6 to 13 carbon atoms or the radical of a nitrogen-containing 6 to 8-membered ring.

The preferred compounds are obtained by reacting maleic acid anhydride and ammonia, methylamine, dimethylamine, dibutylamine, aniline, N-methyl aniline, 4,4'-diaminodiphenyl methane, 4,4'-diaminodiphenyl ether, 2,4-diaminotoluene, 1,5-diaminotoluene, benzylamine, cyclohexylamine, hexamethylene diamine, tris-[aminophenyl]-methane, piperidine and morpholine.

The monoisocyanates used in accordance with the invention are aliphatic and aromatic compounds, optionally substituted by hetero atoms, with one NCO-group in the molecule, for example alkyl isocyanates, such as ethyl, methyl, butyl, dodecyl and stearyl isocyanate, aromatic, optionally substituted monoisocyanates, such as phenyl, tolyl, isopropyl, nonyl isocyanate, nitro, alkoxy, aroxy, chloro, dichloro, trichloro, tetrachloro, pentachloro, benzyl, bromophenyl isocyanate or isocyanatobenzoic acid esters, phthalic acid esters, isophthalic acid esters, isocycanatobenzonitrile, cycloaliphatic isocyanates, such as cyclohexyl isocyanate and unsaturated isocyanates, such as allyl, oleyl or cyclohexenyl isocyanate.

Other starting components suitable for use in accordance with the invention are aliphatic, cycloaliphatic, araliphatic, aromatic and heterocyclic polyisocyanate, preferably diisocyanates (cf. Annalen, 562, pages 75 to 136), for example ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3- and -1,4-diisocyanate and any mixtures of these isomers, 1-isocyanato-3,3,5-trimethyl-5-isocyanatomethyl cyclohexane (German Auslegeschrift No. 1,202,785), 2,4- and 2,6-hexahydrotolylene diisocyanate and any mixtures of these isomers, hexahydro-1,3-and/or -1,4-phenylene diisocyanate, perhydro-2,4'- and/or -4,4'-diphenyl methane diisocyanate, 1,3-and 1,4-phenylene diisocyanate, 2,4- and 2,6-tolylene diisocyanate and any mixtures of these isomers, diphenyl methane-2,4'- and/or 4,4'-diisocyanate, naphthylene-1,5-diisocyanate, triphenyl methane-4,4',4''-triisocyanate, polyphenyl-polymethylene polyisocyanates of the type obtained by condensing aniline with formaldehyde, followed by phosgenation, and described for example in British Patent Specifications Nos. 874,430 and 848,671, perchlorinated aryl polyisocyanates of the type described, for example, in German Auslegeschrift No. 1,157,601, polyisocyanates containing carbodiimide groups of the type described in German Patent Specification No. 1,092,007, diisocyanates of the type described in U.S. Pat. No. 3,492,330, polyisocyanates containing allophanate groups of the type described, for example, in British Patent Specification No. 99,890, in Belgian Patent Specification No. 761,626 and in Published Dutch Patent Application No. 7,102,524, polyisocyanates containing isocyanurate groups of the type described, for example, in German Patent Specifications Nos. 1,022,789; 1,222,067 and 1,027,394 and in German Offenlegungsschrifts Nos. 1,929,034 and 2,004,048, polyisocyanates containing urethane groups of the type described, for example, in Belgian Patent Specification No. 752,261 or in U.S. Pat. No. 3,394,164, polyisocyanates containing acylated urea groups according to German Patent Specification No. 1,230,778, polyisocyanates containing biuret groups of the type described, for example, in German Patent Specification No. 1,101,394, in British Patent Specification No. 889,050 and in French Patent Specification No. 7,017,514, polyisocyanates produced by telomerisation reactions of the type described, for example, in Belgian Patent Specification No. 723,640, polyisocyanates containing ester groups of the type described, for example, in British Patent Specifications Nos. 956,474 and 1,072,956, in U.S. Pat. No. 3,567,763 and in German Patent Specification No. 1,231,688 and reaction products of the above-mentioned isocyanates with acetylene according to German Patent Specification No. 1,072,358.

It is also possible to use the distillation residues containing isocyanate groups which are obtained in the commercial manufacture of isocyanates, optionally in solution in one or more of the above-mentioned polyisocyanates. Any mixtures of the above-mentioned polyisocyanates may also be used.

It is preferred to use mono and poly-iso(thio)cyanates corresponding to the general formula:

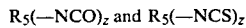

in which $R_5$ represents an optionally substituted aliphatic radical containing from 1 to 20 carbon atoms, an optionally substituted aromatic radical containing from 4 to 20, preferably 6-16, carbon atoms, an optionally substituted cycloaliphatic radical containing from 5 to 12 carbon atoms, an optionally substituted aliphatic-aromatic radical containing from 6 to 20 carbon atoms, and an optionally substituted aromatic or cycloaliphatic radical containing from 4 to 12 carbon atoms and hetero atoms such as N, O or S. The radicals may be substituted by halogen, preferably chlorine, alkyl with $C_1-C_{10}$ and/or aryl groups with $C_6-C_{16}$.

Particularly preferred radicals are aliphatic radicals containing from 2 to 12 carbon atoms or an aryl radical, containing from 6 to 20 carbon atoms, such as phenyl, tolyl, naphthyl, diphenyl methane and diphenyl ether radicals. z is an integer from 1 to 4, preferably from 1 to 3, most preferably 1 or 2.

It is preferred to use the commercially readily obtainable mixtures of tolylene diisocyanates, m-phenylene diisocyanate, phenyl isocyanate and its substitution products and also phosgenated condensates of aniline and formaldehyde with a polyphenylene-methylene structure and the symmetrical compounds 4,4'-diisocyanatodiphenyl methane, 4,4'-diisocyanatodiphenyl ether, p-phenylene diisocyanate, 4,4'-diisocyanatodiphenyl dimethyl methane, analogous hydroaromatic diisocyanates, aliphatic diisocyanates with 2 to 12 carbon atoms such as hexamethylene diisocyanate and diisocyanates derived from isophorone.

The isocyanates may be used in the free form and also partly or completely in the form of their derivatives which are obtained by reaction with compounds containing reactive hydrogen and which react as masked isocanates under the reaction conditions.

Preferred donors are the acyl ureas obtainable from lactams, for example caprolactam, and the carbamic acid esters obtained from aromatic and aliphatic mono- and polyhydroxy compounds which correspond for example to the general formulae:

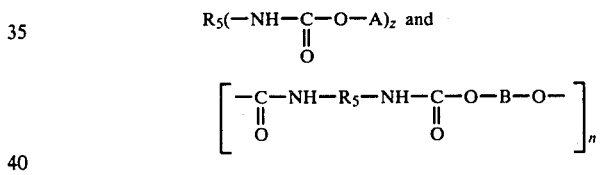

in which $R_5$ and z are as defined above, A represents the organic radical of a monohydroxy compound, B represents the organic radical of a bis- or tris-functional hydroxy compound, perferably both, A and B the same or different, an aliphatic radical containing from 1 to 10 carbon atoms, a cycloaliphatic radical containing from 5 to 10 carbon atoms, an aliphatic-aromatic radical containing from 7 to 20 carbon atoms and an aromatic radical with 6 to 12 carbon atoms which, in each case, may also be substituted by alkyl and/or aryl groups, and n is an integer from 1 to 1000, preferably from 1 to 100.

Examples of these carbamic acid esters are the carbamic acid esters of phenol, isomeric cresols, their commercial mixtures and similar aromatic hydroxyl compounds, aliphatic monoalcohols such as methanol, ethanol, propanol, isopropanol, butanol, isobutanol, diethylene glycol monomethyl ether, cyclohexanol, benzyl alcohol and aliphatic diols or polyols, such as ethylene glycol and trimethylol propane.

The urethanes may be used as such or may be formed in situ by reaction with alcohols.

Instead of using the above-mentioned (poly)isocyanates, it is also possible to use the analogous (poly)isothiocyanates.

The reaction according to the invention is illustrated by the following reaction scheme:

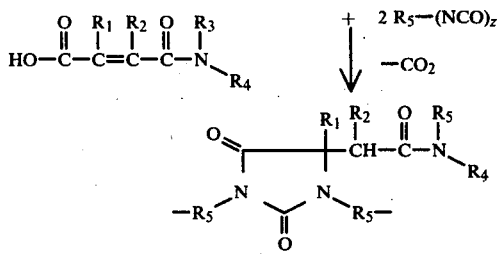

in which
the radicals $R_1$ to $R_5$ are as defined above;
where $z=1$, a monomolecular compound is formed and, where $z>1$, a higher molecular compound is formed, the hydantoin rings being attached through the radicals $R_5$—.

Accordingly, the present invention also provides monomolecular hydantoins corresponding to the general formula (I):

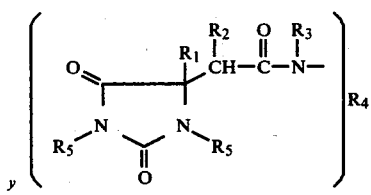

and higher molecular hydantoins which contain the recurring structural unit corresponding to the general formula (II):

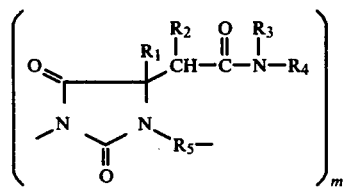

In the general formulae (I) and (II) above, the radicals $R_1$, $R_2$, $R_3$, $R_4$ and $R_5$ and also y are as defined above with the exception that $R_4$ need not by hydrogen and m is an integer from 2 to 1000, preferably from 2 to 100.

The hydantoins according to the invention may be clearly identified by IR-spectra in which the bands characteristic of hydantoins and amides appear. The higher molecular hydantoins have a solution viscosity of from 300 to 200,000 mPa.s, preferably from 1000 to 50,000 mPa.s, as determined on a 30% by weight solution in butyrolactone at a temperature of up to 25° C.

The reaction according to the invention may be carried out in solvents which do not react under the reaction conditions or only form loose addition compounds, or even in an excess of one of the reaction components. Suitable solvents are (halogenated) hydrocarbons, phenols, esters, lactones, ketones, ethers, substituted amides, nitriles, phosphoric acid amides, sulphoxides and sulphones, for example xylenes, o-dichlorobenzene, phenol, cresols, benzoic acid alkyl esters, butyrolactone, caprolactone, acetophenone, cyclohexanone, glycol monomethyl ether acetate, diethylene glycol monoethyl ether, dimethyl formamide, N-methyl pyrrolidone, caprolactam, benzonitrile, hexamethyl phosphoric acid triamide, dimethyl sulphoxide, tetramethylene sulphone and mixtures thereof.

The process according to the invention is carried out by keeping the reaction components with or without solvent at temperatures of from about 0 to 450° C. and preferably at temperatures of from 0 to 250° C. over periods ranging from a few minutes to several hours. The progress of the reaction may be followed from the evolution of gas and the IR-spectra. In some cases, it is advantageous to carry out the reaction in several stages or to add the individual components in a different order or at different temperatures. It is also possible, especially in the production of polymers, to prepare a condensation product in a first step, for example in a solvent, and then to convert this condensation product into the high molecular weight product, for example a lacquer film, at elevated temperatures with chain extension or crosslinking and, optionally, evaporation of the solvent. When used in lacquers, these condensation products may even be applied from melts or aqueous dispersions.

In general, 2 vals of isocyanate are used per val of amido acid, although appreciable deviations preferably up to 100% excess of each reaction component from these quantitative ratios are also possible. Monomolecular hydantoins are obtained from monofunctional amido acids and monofunctional isocyanates, higher molecular polyhydantoins are obtained from monofunctional amido acids and diisocyanates and crosslinked hydantoins or hydantoin isocyanates are obtained from oligofunctional amido acids and isocyanates, depending upon the stoichiometric ratios.

In another embodiment, polycarboxylic acids and polyols, for example, are also used in the production of polyhydantoins in accordance with the invention, whereby ester groups are incorporated. Examples of this are the condensation of terephthalic acid dimethyl ester with ethylene glycol, glycerol and tris-hydroxyethyl-isocyanurate to form a polyester. The quantitative ratios in which these additions are used may fluctuate within wide limits, quantities of from 10 to 400% by weight, based on the condensate according to the invention, being preferred.

The reaction according to the invention may be influenced by catalysts, for example amines such as triethylamine, 1,4-diazabicyclo-(2,2,2)-octane, N-ethyl morpholine and N-methyl imidazole, organic and inorganic metal compounds, especially those of iron, lead, zinc, tin, copper, cobalt and titanium, such as iron(III)chloride, cobalt acetate, lead oxide, lead acetate, zinc octoate, dibutyl tin dilaurate, copper acetyl acetonate and titanium tetrabutylate and phosphorus compounds, such as trialkyl phosphine and 1-methyl phospholine oxide.

The monomolecular hydantoins obtainable by the process according to the invention show activity in the pharmaceutical and plant-protection fields. They may be also used to improve the flowing properties of lacquers.

The polyhydantoins according to the invention are distinguished by their outstanding thermal stability and are suitable for use as adhesives lacquers, films and shaped articles. Their properties may be varied within wide limits for the various applications envisaged by the addition of fillers, pigments and low molecular weight and high molecular weight components, for example for the production of lacquers and films by admixture with polyesters and polycarbamic esters.

EXAMPLE 1

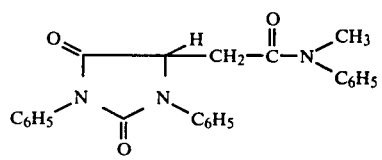

103 g of the amido acid of maleic acid anhydride and N-methyl aniline are dissolved in 200 g of butyrolactone. 119 g of phenyl isocyanate are then added dropwise at 20° to 25° C. 0.2 g of triethylene diamine are then added and the mixture is stirred for 2 hours at 50° C., for 2 hours at 100° C. and for 4 hours at 150° C. The condensation and ring-forming reaction are accompanied by the elimination of carbon dioxide. On completion of the reaction, 112 g of the hydantoin melting at 191° C. crystallise out on cooling. Another 17 g are obtained from the filtrate by precipitation with water and recrystallisation from ethanol/dioxane (3:1). After another recrystallisation from ethanol/dioxane, 1,3-diphenyl-5-(N-methyl-N-phenylaminocarbonylmethyl)-hydantoin is obtained in the form of almost colourless crystals melting at 195° to 196° C. In the IR-spectrum, the compound shows the bands typical of hydantoins at 1720 and 1780 cm$^{-1}$ and a band corresponding to amide at 1645 cm$^{-1}$.

| $C_{24}H_{21}N_3O_3$ (399) | C | H | N |
|---|---|---|---|
| calculated: | 72.2 | 5.3 | 10.5% |
| observed: | 72.2 | 5.2 | 10.4%. |

EXAMPLE 2

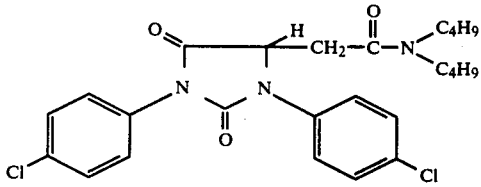

110 g of the N,N-dibutylamido acid of maleic acid anhydride in 100 g of butyrolactone are added dropwise at 20° C. to a solution of 154 g of 4-chlorophenyl isocyanate in 100 g of butyrolactone. The reaction is weakly exothermic. The reaction mixture is then stirred for 1 hour at 50° C., for 4 hours at 100° C., for 2 hours at 150° C. and for 3 hours at 180° C. 171 g of 1,3-bis-(4-chlorophenyl)-5-(N,N-dibutylaminocarbonyl-methyl)-hydantoin melting at 124° C. are obtained on cooling. After recrystallisation from ethanol/dioxane, this compound gives colourless crystals melting at 145° C. and with IR bands at 1715 and 1775 cm$^{-1}$ for hydantoin and at 1645 cm$^{-1}$ for amide.

| $C_{25}H_{29}Cl_2N_3O_3$ (489.9) | C | H | N |
|---|---|---|---|
| calculated: | 61.2 | 5.9 | 8.5% |
| observed: | 61.3 | 6.1 | 8.3% |

EXAMPLE 3

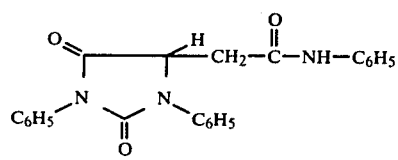

93 g of aniline are added dropwise with cooling at approximately 30° C. to a solution of 98 g of maleic acid anhydride in 300 g of N-methyl pyrrolidone. To complete the formation of the amido acid, the mixture is then stirred for 1 hour at the above-mentioned temperature. 238 g of phenyl isocyanate are then added dropwise at 20° C. and the condensation reaction is carried out with stirring for 1 hour at 50° C., for 2 hours at 90° C., for 2 hours at 120° C. and for 6 hours at 150° C. The reaction product crystallises out on cooling and is recrystallised from acetonitrile and from metahnol. 1,3-Diphenyl-5-(N-phenylaminocarbonylmethyl)-hydantoin is obtained in the form of colourless crystals melting at 214° to 215° C.

| $C_{23}H_{19}N_3O_3$ (385) | C | H | N |
|---|---|---|---|
| calculated: | 71.7 | 4.9 | 10.9% |
| observed: | 72.0 | 5.1 | 10.6%. |

EXAMPLE 4

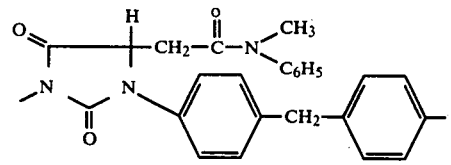 (I)

103 g of the amido acid of N-methyl aniline and maleic acid anhydride are dissolved in 450 g of butyrolactone, followed by the addition in portions at 25° C. of 130 g of 4,4'-diisocyanatodiphenyl methane. The temperature is then increased in stages and the reaction mixture is stirred for 2 hours at 50° C., for 2 hours at 100° C., for 2 hours at 120° C. and for 11 hours at 150° C. An approximately 30% solution of polyhydantoin of the above defined recurring structural unit (I) is obtained. It has a viscosity $\eta^{25}$ of 3900 mPas and, in the IR spectrum, shows a band corresponding to amides at 1655 cm$^{-1}$ and the bands corresponding to hydantoins at 1720 and 1775 cm$^{-1}$.

Part of the polyhydantoin solution is coated onto a metal plate and is stoved at 200° to 300° C. to form an elastic lacquer film.

We claim:

1. A process for producing hydantoins wherein an organic diisocyanate, diisothiocyanate, polyisocyanate or polyisothiocyanate is reacted with an unsaturated amido acid corresponding to the general formula

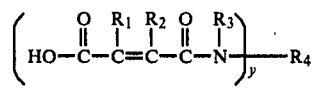

in which the radicals

R₁, R₂, R₃ and R₄ are same or different and represent hydrogen, an aliphatic, aliphatic-aromatic or aromatic radical, and R₁ and R₂ may additionally represent halogen, and y is an integer from 1 to 3, at a temperature of from 0° to 450° C.

2. Processes as claimed in claim 1, wherein a monofunctional unsaturated amido acid and an at least bisfunctional organic isocyanate or isothiocyanate are used.

3. Processes as claimed in claim 1, wherein an at least bisfunctional unsaturated amido acid and an at least bisfunctional organic isocyanate or isothiocyanate are used as starting materials.

4. Processes as claimed in claim 1, wherein in the general formula R₁, R₂, R₃ and R₄ represent hydrogen, an aliphatic radical with 1 to 20 carbons an aliphatic-aromatic radical with 7 to 20 C-atoms or an aromatic radical with 4 to 20 C-atoms.

5. Processes as claimed in claim 1, wherein the unsaturated amido acid is the reaction product of maleic acid anhydride with ammonia, methylamine, dimethylamine, dibutylamine, aniline, N-Methyl aniline, 4,4'-diaminodiphenyl methane, 4,4'-diaminodiphenyl ether, 2,4-diaminotoluene, 1,5-diamino-toluene, benzylamine, cyclohexylamine, hexamethylene diamine, tris-(aminophenyl)-methane, piperidine or morpholine.

6. Processes as claimed in claim 1, wherein the isocyanates or isothiocyanates are R₅—(NCO)_z and R₅(—NCS)_z in which R₅ represents an optionally substituted aliphatic radical containing from 1 to 20 carbon atoms, optionally substituted by halogen, alkyl and/or aryl groups, an optionally substituted aromatic radical containing from 6 to 12 carbon atoms, an optionally substituted cycloaliphatic radical containing from 5 to 12 carbon atoms, an optionally substituted aliphatic-aromatic radical containing from 6 to 20 carbon atoms, or an optionally substituted aromatic or cycloaliphatic radical containing from 4 to 12 carbon atoms and hetero atoms such as N, O or S, and z is an integer from 2 to 4, are used.

7. An oligomeric or polymeric hydantoin of the m-times recurring structural unit corresponding to the general formula (II):

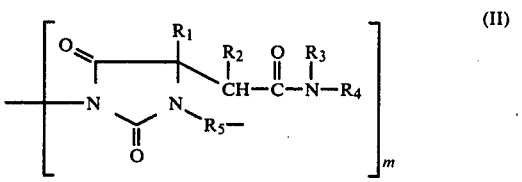

in which

R₁, R₂, R₃ and R₄, which may be the same or different, represent hydrogen, an aliphatic, aliphatic-aromatic or aromatic radical and R₁ and R₂ may additionally represent halogen, R₅ is unsubstituted or substituted aliphatic of 1–20 carbon atoms, unsubstituted or substituted aryl of 4–20 carbon atoms, or unsubstituted or substituted cycloaliphatic of 5–20 carbon atoms, and m is an integer from 2 to 1000.

8. A temperature-resistant lacquer, film, adhesive or shaped article comprising a polyhydantoin as claimed in claim 7.

* * * * *